United States Patent
Xu et al.

(10) Patent No.: US 12,273,683 B2
(45) Date of Patent: Apr. 8, 2025

(54) SELF-FIT HEARING INSTRUMENTS WITH SELF-REPORTED MEASURES OF HEARING LOSS AND LISTENING

(71) Applicant: Starkey Laboratories, Inc., Eden Prairie, MN (US)

(72) Inventors: Jingjing Xu, Eden Prairie, MN (US); Tao Wu, Edina, MN (US); Karrie Recker, Edina, MN (US); Jeffery Lee Crukley, Milton (CA)

(73) Assignee: Starkey Laboratories, Inc., Eden Prairie, MN (US)

( * ) Notice: Subject to any disclaimer, the term of this patent is extended or adjusted under 35 U.S.C. 154(b) by 643 days.

(21) Appl. No.: 17/603,872

(22) PCT Filed: Apr. 9, 2020

(86) PCT No.: PCT/US2020/027484
§ 371 (c)(1),
(2) Date: Oct. 14, 2021

(87) PCT Pub. No.: WO2020/214482
PCT Pub. Date: Oct. 22, 2020

(65) Prior Publication Data
US 2022/0201404 A1 Jun. 23, 2022

Related U.S. Application Data

(60) Provisional application No. 62/887,369, filed on Aug. 15, 2019, provisional application No. 62/835,886, filed on Apr. 18, 2019.

(51) Int. Cl.
*G16H 10/20* (2018.01)
*A61B 5/12* (2006.01)
*H04R 25/00* (2006.01)

(52) U.S. Cl.
CPC ........... *H04R 25/305* (2013.01); *A61B 5/123* (2013.01); *G16H 10/20* (2018.01); *H04R 25/70* (2013.01); *H04R 2225/43* (2013.01)

(58) Field of Classification Search
CPC ...... A61B 5/123; G16H 10/20; H04R 25/305; H04R 25/70; H04R 2225/43
See application file for complete search history.

(56) References Cited

U.S. PATENT DOCUMENTS

| | | | |
|---|---|---|---|
| 7,650,004 | B2 | 1/2010 | Durant |
| 8,355,794 | B2 | 1/2013 | Lineaweaver et al. |

(Continued)

FOREIGN PATENT DOCUMENTS

| | | | |
|---|---|---|---|
| EP | 2071875 A2 | 6/2009 | |
| EP | 3468227 A1 | 4/2019 | |

(Continued)

OTHER PUBLICATIONS

Kochkin et al., "The validity and reliability of the BHI Quick Hearing Check", Hearing Review, Nov. 1, 2010, 8 pp.

(Continued)

*Primary Examiner* — Benjamin S Melhus
*Assistant Examiner* — Nidhi N Patel
(74) *Attorney, Agent, or Firm* — Shumaker & Sieffert, P.A.

(57) ABSTRACT

A processing system is configured to obtain data indicating answers of a user of one or more hearing instruments to a (Continued)

questionnaire. Additionally, the processing system is configured to determine an initial audiogram based on the answers. Furthermore, the processing system is configured to perform an initial fitting of the one or more hearing instruments based on the initial audiogram.

20 Claims, 8 Drawing Sheets

(56) References Cited

U.S. PATENT DOCUMENTS

| | | | |
|---|---|---|---|
| 8,718,288 | B2 | 5/2014 | Woods et al. |
| 10,896,020 | B2 | 1/2021 | Christiansen et al. |
| 2013/0085411 | A1 | 4/2013 | Van Tasell |
| 2014/0241537 | A1* | 8/2014 | Krause .......... H04R 25/70 381/60 |
| 2015/0023512 | A1 | 1/2015 | Shennib |
| 2015/0023534 | A1 | 1/2015 | Shennib |
| 2015/0023535 | A1 | 1/2015 | Shennib |
| 2017/0164124 | A1 | 6/2017 | Shennib |
| 2017/0171046 | A1* | 6/2017 | Flood .......... H04B 1/385 |

FOREIGN PATENT DOCUMENTS

| | | |
|---|---|---|
| WO | 2009/026959 A1 | 3/2009 |
| WO | 2010/066305 A1 | 6/2010 |
| WO | 2013017169 A1 | 2/2013 |

OTHER PUBLICATIONS

Bisgaard et al., "Standard audiograms for the IEC 60118-15 measurement procedure", Trends in amplification, vol. 14, Jun. 2010, pp. 113-120.

International Search Report and Written Opinion of International Application No. PCT/US2020/027484, mailed Aug. 10, 2020, 15 pp.

International Preliminary Report on Patentability from International Application No. PCT/US2020/027484, mailed Oct. 28, 2021, pp. 9.

Smoorenburg, "Speech reception in quiet and in noisy conditions by individuals with noise-induced hearing loss in relation to their tone audiogram", Journal of the Acoustical Society of America, Jan. 1992, 17 pp.

Urbanski, "Development of Evidence-Based Gain-Frequency Responses for Preconfigured OTC Hearing Aids", The University of Iowa, Feb. 28-Mar. 2, 2019, 2 pp.

Staab. "Hearin Self-Test", Hearing Health and Technology Matters, Apr. 18, 2017, 10 pp.

* cited by examiner

Loudness balance

1. Right ear much louder
2. Right ear slightly loud
3. The same loudness
4. Left ear slightly louder
5. Left ear much louder

FIG. 7

CATEGORIES OF LOUDNESS

7. UNCOMFORTABLY LOUD
6. LOUD, BUT O.K.
5. COMFORTABLE, BUT SLIGHTLY LOUD
4. COMFORTABLE
3. COMFORTABLE, BUT SLIGHTLY SOFT
2. SOFT
1. VERY SOFT

FIG. 8

Clarity

1. Boomy
2. Slightly boomy
3. Clear
4. Slightly Tinny
5. Tinny

SELF-FIT HEARING INSTRUMENTS WITH SELF-REPORTED MEASURES OF HEARING LOSS AND LISTENING

CROSS-REFERENCE TO RELATED APPLICATION

This application is a national stage application under 35 U.S.C. § 371 of PCT Application No. PCT/US2020/027484, filed Apr. 9, 2020, which claims the benefit of U.S. Provisional Application No. 62/835,886 filed Apr. 18, 2019 and U.S. Provisional Application No. 62/887,369 filed Aug. 15, 2019. The entire contents of each of PCT Application No. PCT/US2020/027484 and U.S. Provisional Application No. 62/835,886 and U.S. Provisional Application No. 62/887,369 are incorporated herein by reference in their entirety.

TECHNICAL FIELD

This disclosure relates to hearing instruments.

BACKGROUND

Hearing instruments are devices designed to be worn on, in, or near one or more of a user's ears. Common types of hearing instruments include heating assistance devices (e.g., "hearing aids"), earbuds, headphones, hearables, cochlear implants, and so on. In some examples, a hearing instrument may be implanted or osseointegrated into a user. Some hearing instruments include additional features beyond just environmental sound-amplification. For example, some modern hearing instruments include advanced audio processing for improved device functionality, controlling and programming the devices, and beamforming, and some can even communicate wirelessly with external devices including other hearing instruments (e.g., for streaming media).

SUMMARY

This disclosure describes techniques for self-fitting of hearing instruments with self-reported measures of hearing loss and listening perception. Over-the-counter (OTC) and direct-to-consumer (DTC) heating aid users are facing many technical challenges with existing self fitting strategies, especially for older users. Strategies that are intuitive to these users are desirable. In this disclosure, techniques to self-fit hearing aids based on self-reported measures of hearing loss and listening perception are introduced. By filling out a short questionnaire and answering a few questions after listening with the OTC/DTC hearing aids, a user may be able to self-program the hearing aids to compensate his/her hearing loss with satisfaction. Although some portions of this disclosure describe examples with respect to hearing aids, such examples may apply to other types of hearing instruments.

In one example, this disclosure describes a method comprising: obtaining, by a processing system, data indicating answers of a user of one or more hearing instruments to a questionnaire; determining, by the processing system, an initial audiogram based on the answers; and performing, by the processing system, an initial fitting of the one or more hearing instruments based on the initial audiogram.

In another example, this disclosure describes a computing system comprising: one or more computing devices, wherein one or more processors and one or more communication units are included in the one or more computing devices, the one or more communication units are configured to communicate with one or more hearing instruments, and the one or more processors are configured to: obtain data indicating answers of a user of the one or more hearing instruments to a questionnaire; determine an initial audiogram based on the answers; and perform an initial fitting of the one or more hearing instruments based on the initial audiogram.

In another example, this disclosure describes one or more processors configured to: obtain data indicating answers of a user of the one or more hearing instruments to a questionnaire; determine an initial audiogram based on the answers; and perform an initial fitting of the hearing instrument based on the initial audiogram; and a receiver comprising one or more speakers for generating audible sound.

In another example, this disclosure describes a computer-readable data storage medium having instructions stored thereon that when executed cause a processing system to: obtain data indicating answers of a user of one or more heating instruments to a questionnaire; determine an initial audiogram based on the answers; and perform an initial fitting of the one or more hearing instruments based on the initial audiogram.

The details of one or more aspects of the disclosure are set forth in the accompanying drawings and the description below. Other features, objects, and advantages of the techniques described in this disclosure will be apparent from the description, drawings, and claims.

BRIEF DESCRIPTION OF DRAWINGS

FIG. 7 is an example scale for measuring self-reported loudness balance between two ears, accordance with one or more aspects of this disclosure.

FIG. 8 is an example scale for measuring self-reported overall loudness, in accordance with one or more aspects of this disclosure.

DETAILED DESCRIPTION

Figure 1:
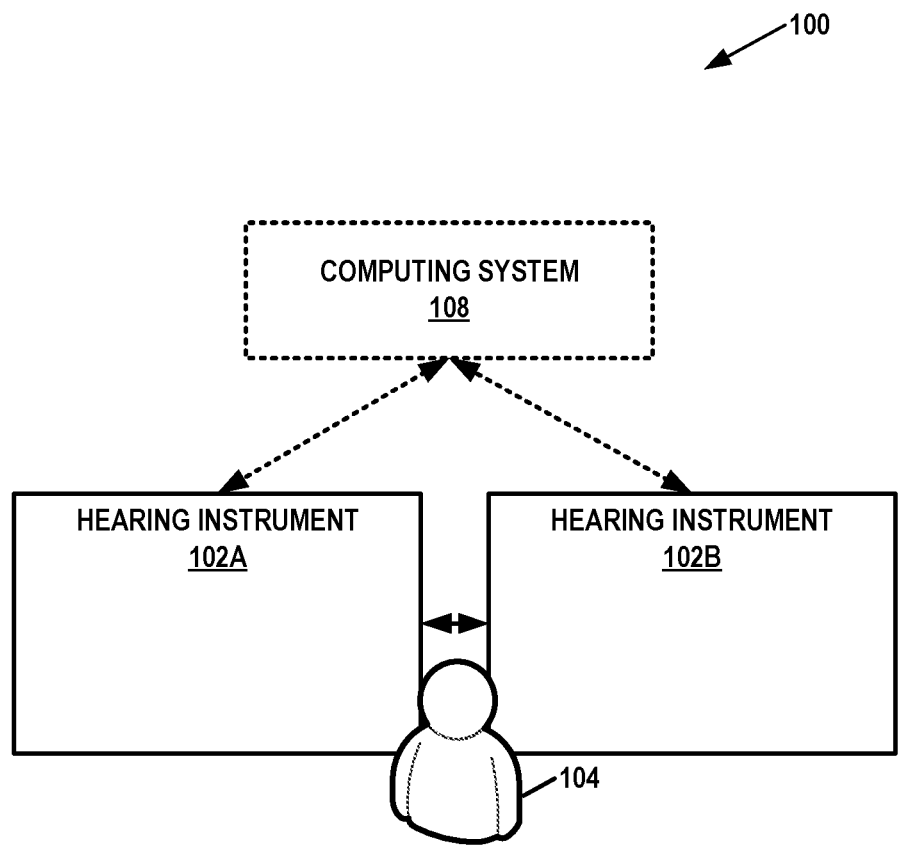
FIG. 1 is a conceptual diagram illustrating an example system that includes one or more hearing instrument(s), in accordance with one or more techniques of this disclosure.

FIG. 1 is a conceptual diagram illustrating an example system 100 that includes hearing instruments 102A, 102B, in accordance with one or more techniques of this disclosure. This disclosure may refer to hearing instruments 102A and 102B collectively, as "hearing instruments 102." A user 104 may wear hearing instruments 102. In some instances, such as when user 104 has unilateral hearing loss, user 104 may wear a single hearing instrument. In other instances, such as when user 104 has bilateral hearing loss, the user may wear two hearing instruments, with one hearing instrument for each ear of the user.

Hearing instruments 102 may comprise one or more of various types of devices that are configured to provide auditory stimuli to a user and that are designed for wear and/or implantation at, on, or near an ear of the user. Hearing instruments 102 may be worn, at least partially, in the ear canal or concha. One or more of hearing instruments 102 may include behind the ear (BTE) components that are worn behind the ears of user 104. In some examples, hearing instruments 102 comprise devices that are at least partially implanted into or osseointegrated with the skull of the user. In some examples, one or more of hearing instruments 102 is able to provide auditory stimuli to user 104 via a bone conduction pathway.

In any of the examples of this disclosure, each of hearing instruments 102 may comprise a hearing assistance device. Hearing assistance devices include devices that help a user hear sounds in the user's environment. Example types of hearing assistance devices may include hearing aid devices, Personal Sound Amplification Products (PSAPs), cochlear implant systems (which may include cochlear implant magnets, cochlear implant transducers, and cochlear implant processors), and so on. In some examples, hearing instruments 102 are over-the-counter, direct-to-consumer, or prescription devices. Furthermore, in some examples, hearing instruments 102 include devices that provide auditory stimuli to the user that correspond to artificial sounds or sounds that are not naturally in the user's environment, such as recorded music, computer-generated sounds, or other types of sounds. For instance, hearing instruments 102 may include so-called "hearables," earbuds, earphones, or other types of devices. Some types of hearing instruments provide auditory stimuli to the user corresponding to sounds from the user's environment and also artificial sounds.

In some examples, one or more of hearing instruments 102 includes a housing or shell that is designed to be worn in the ear for both aesthetic and functional reasons and encloses the electronic components of the hearing instrument. Such hearing instruments may be referred to as in-the-ear (ITE), in-the-canal (ITC), completely-in-the-canal (CIC), or invisible-in-the-canal (IIC) devices. In some examples, one or more of hearing instruments 102 may be behind-the-ear (BTE) devices, which include a housing worn behind the ear that contains all of the electronic components of the hearing instrument, including the receiver (i.e., the speaker). The receiver conducts sound to an earbud inside the ear via an audio tube. In some examples, one or more of hearing instruments 102 may be receiver-in-canal (RIC) hearing-assistance devices, which include a housing worn behind the ear that contains electronic components and a housing worn in the ear canal that contains the receiver.

Hearing instruments 102 may implement a variety of features that help user 104 hear better. For example, hearing instruments 102 may amplify the intensity of incoming sound, amplify the intensity of certain frequencies of the incoming sound, or translate or compress frequencies of the incoming sound. In another example, hearing instruments 102 may implement a directional processing mode in which hearing instruments 102 selectively amplify sound originating from a particular direction (e.g., to the front of the user) while potentially fully or partially canceling sound originating from other directions. In other words, a directional processing mode may selectively attenuate off-axis unwanted sounds. The directional processing mode may help users understand conversations occurring in crowds or other noisy environments. In some examples, hearing instruments 102 may use beamforming or directional processing cues to implement or augment directional processing modes.

In some examples, hearing instruments 102 may reduce noise by canceling out or attenuating certain frequencies. Furthermore, in some examples, hearing instruments 102 may help user 104 enjoy audio media, such as music or sound components of visual media, by outputting sound based on audio data wirelessly transmitted to hearing instruments 102.

Hearing instruments 102 may be configured to communicate with each other. For instance, in any of the examples of this disclosure, hearing instruments 102 may communicate with each other using one or more wirelessly communication technologies. Example types of wireless communication technology include Near-Field Magnetic Induction (NFMI) technology, a 900 MHz technology, a BLUETOOTH™ technology, a WI-FI™ technology, audible sound signals, ultrasonic communication technology, infrared communication technology, an inductive communication technology, or another type of communication that does not rely on wires to transmit signals between devices. In some examples, hearing instruments 102 use a 2.4 GHz frequency band for wireless communication. In some examples of this disclosure, hearing instruments 102 may communicate with each other via non-wireless communication links, such as via one or more cables, direct electrical contacts, and so on.

As shown in the example of FIG. 1, system 100 may also include a computing system 108. In other examples, system 100 does not include computing system 108. Computing system 108 comprises one or more computing devices, each of which may include one or more processors. For instance, computing system 108 may comprise one or more mobile devices, server devices, personal computer devices, handheld devices, wireless access points, smart speaker devices, smart televisions, medical alarm devices, smart key fobs, smartwatches, smartphones, motion or presence sensor devices, smart displays, screen-enhanced smart speakers, wireless routers, wireless communication hubs, prosthetic devices, mobility devices, special-purpose devices, accessory devices, and/or other types of devices. Accessory devices may include devices that are configured specifically for use with hearing instruments 102. Example types of accessory devices may include charging cases for hearing instruments 102, storage cases for hearing instruments 102, media streamer devices, phone streamer devices, external microphone devices, remote controls for hearing instruments 102, and other types of devices specifically designed for use with hearing instruments 102. Actions described in this disclosure as being performed by computing system 108 may be performed by one or more of the computing devices of computing system 108. One or more of hearing instruments 102 may communicate with computing system 108 using wireless or non-wireless communication links. For instance, hearing instruments 102 may communicate with computing system 108 using any of the example types of communication technologies described elsewhere in this disclosure.

Figure 2:
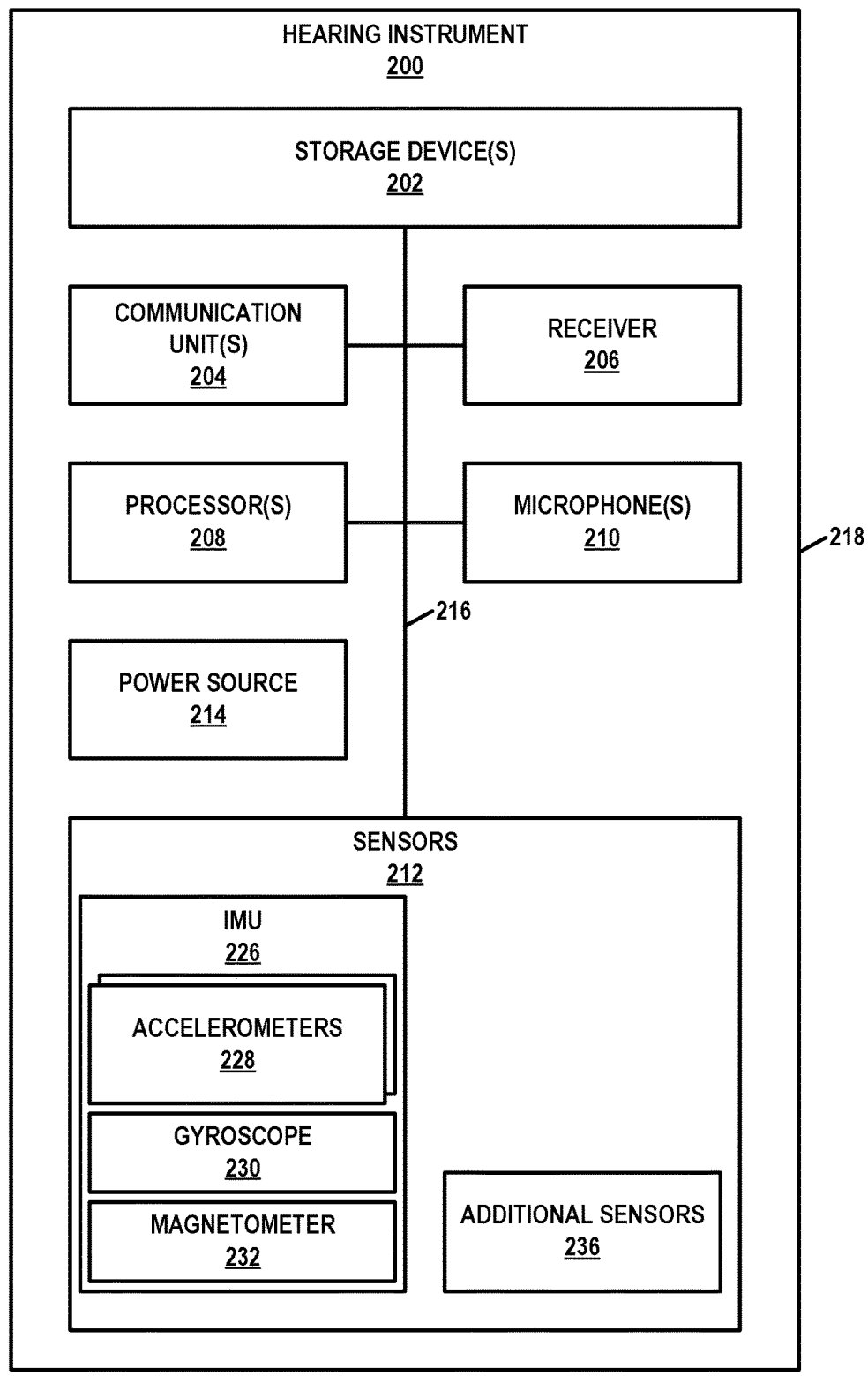
FIG. 2 is a block diagram illustrating example components of a hearing instrument, in accordance with one or more aspects of this disclosure.

FIG. 2 is a block diagram illustrating example components of hearing instrument 200, in accordance with one or more aspects of this disclosure. Hearing instrument 200 may be either one of hearing instruments 102 (FIG. 1). In the example of FIG. 2, hearing instrument 200 comprises one or more storage devices 202, one or more communication units 204, a receiver 206, one or more processors 208, one or more microphones 210, a set of sensors 212, a power source 214, and one or more communication channels 216. Communication channels 216 provide communication between storage devices 202, communication unit(s) 204, receiver 206, processor(s) 208, a microphone(s) 210, and sensors 212. Components 202, 204, 206, 208, 210, and 212 may draw electrical power from power source 214.

In the example of FIG. 2, each of components 202, 204, 206, 208, 210, 212, 214, and 216 are contained within a single housing 218. However, in other examples of this disclosure, components 202, 204, 206, 208, 210, 212, 214, and 216 may be distributed among two or more housings. For instance, in an example where hearing instrument 200 is a RIC device, receiver 206 and one or more of sensors 212 may be include in an in-ear housing separate from a behind-the-ear housing that contains the remaining components of hearing instrument 200. In such examples, a RIC cable may connect the two housings.

Furthermore, in the example of FIG. 2, sensors 212 include an inertial measurement unit (IMU) 226 that is configured to generate data regarding the motion of hearing instrument 200. IMU 226 may include a set of sensors. For instance, in the example of FIG. 2, IMU 226 includes one or more of accelerometers 228, a gyroscope 230, a magnetometer 232, combinations thereof, and/or other sensors for determining the motion of hearing instrument 200. Furthermore, in the example of FIG. 2, hearing instrument 200 may include one or more additional sensors 236. Additional sensors 236 may include a photoplethysmography (PPG) sensor, blood oximetry sensors, blood pressure sensors, electrocardiograph (EKG) sensors, body temperature sensors, electroencephalography (EEG) sensors, environmental temperature sensors, environmental pressure sensors, environmental humidity sensors, skin galvanic response sensors, and/or other types of sensors. In other examples, hearing instrument 200 and sensors 212 may include more, fewer, or different components.

Storage devices 202 may store data. Storage devices 202 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage devices 202 may further be configured for long-term storage of information as non-volatile memory space and may retain information after power on/off cycles. Examples of non-volatile memory configurations may include magnetic hard discs, optical discs, floppy discs, flash memories, or forms of electrically programmable memories (EPROM) or electrically erasable and programmable (EEPROM) memories.

Communication unit(s) 204 may enable hearing instrument 200 to send data to and receive data from one or more other devices, such as another hearing instrument, an accessory device, a mobile device, or another types of device. Communication unit(s) 204 may enable hearing instrument 200 using wireless or non-wireless communication technologies. For instance, communication unit(s) 204 enable hearing instrument 200 to communicate using one or more of various types of wireless technology, such as a BLUETOOTH™ technology, 3G, 4G, 4G LTE, 5G, ZigBee, WI-FI™, Near-Field Magnetic Induction (NFMI), ultrasonic communication, infrared (IR) communication, or another wireless communication technology. In some examples, communication unit(s) 204 may enable hearing instrument 200 to communicate using a cable-based technology, such as a Universal Serial Bus (USB) technology.

Receiver 206 comprises one or more speakers for generating audible sound. Microphone(s) 210 detects incoming sound and generates one or more electrical signals (e.g., an analog or digital electrical signal) representing the incoming sound.

Processor(s) 208 may be processing circuits configured to perform various activities. For example, processor(s) 208 may process the signal generated by microphone(s) 210 to enhance, amplify, or cancel-out particular channels within the incoming sound. Processor(s) 208 may then cause receiver 206 to generate sound based on the processed signal. In some examples, processor(s) 208 include one or more digital signal processors (DSPs). In some examples, processor(s) 208 may cause communication unit(s) 204 to transmit one or more of various types of data. For example, processor(s) 208 may cause communication unit(s) 204 to transmit data to computing system 108. Furthermore, communication unit(s) 204 may receive audio data from computing system 108 and processor(s) 208 may cause receiver 206 to output sound based on the audio data.

Figure 3:
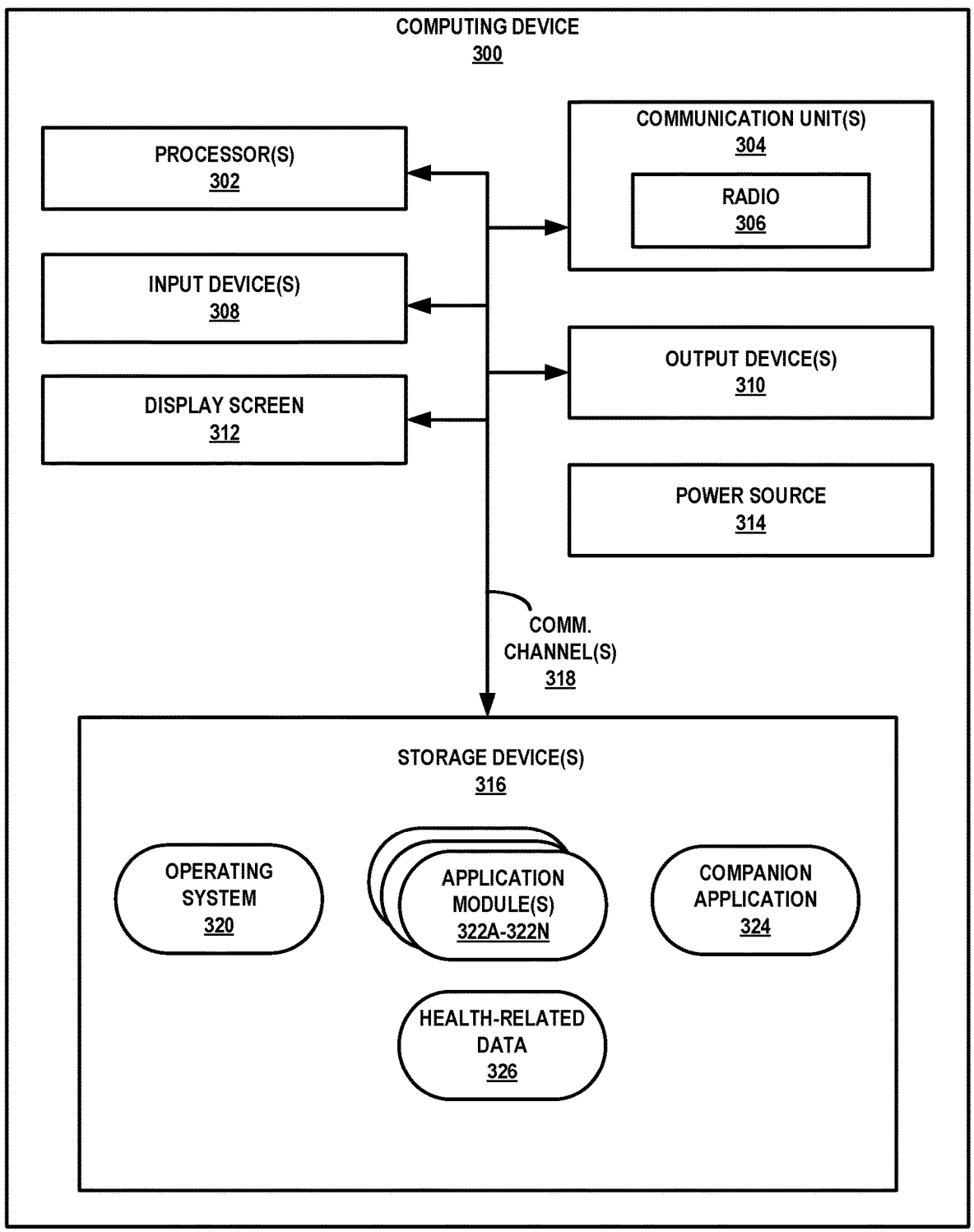
FIG. 3 is a block diagram illustrating example components of a computing device, in accordance with one or more aspects of this disclosure.

FIG. 3 is a block diagram illustrating example components of computing device 300, in accordance with one or more aspects of this disclosure. FIG. 3 illustrates only one particular example of computing device 300, and many other example configurations of computing device 300 exist. Computing device 300 may be a computing device in computing system 108 (FIG. 1).

As shown in the example of FIG. 3, computing device 300 includes one or more processor(s) 302, one or more communication unit(s) 304, one or more input device(s) 308, one or more output device(s) 310, a display screen 312, a power source 314, one or more storage device(s) 316, and one or more communication channels 318. Computing device 300 may include other components. For example, computing device 300 may include physical buttons, microphones, speakers, communication ports, and so on. Communication channel(s) 318 may interconnect each of components 302, 304, 308, 310, 312, and 316 for inter-component communications (physically, communicatively, and/or operatively). In some examples, communication channel(s) 318 may include a system bus, a network connection, an inter-process communication data structure, or any other method for communicating data. Power source 314 may provide electrical energy to components 302, 304, 308, 310, 312 and 316.

Storage device(s) 316 may store information required for use during operation of computing device 300. In some examples, storage device(s) 316 have the primary purpose of being a short term and not a long-term computer-readable storage medium. Storage device(s) 316 may be volatile memory and may therefore not retain stored contents if powered off. Storage device(s) 316 may further be configured for long-term storage of information as non-volatile memory space and may retain information after power on/off cycles. In some examples, processor(s) 302 of computing device 300 may read and execute instructions stored by storage device(s) 316.

Computing device 300 may include one or more input device(s) 308 that computing device 300 uses to receive user input. Examples of user input include tactile, audio, and video user input. Input device(s) 308 may include presence-sensitive screens, touch-sensitive screens, mice, keyboards, voice responsive systems, microphones or other types of devices for detecting input from a human or machine.

Communication unit(s) 304 may enable computing device 300 to send data to and receive data from one or more other computing devices (e.g., via a communications network, such as a local area network or the Internet). For instance, communication unit(s) 304 may be configured to receive data exported by hearing instrument(s) 102, receive data generated by user 104 of hearing instrument(s) 102, receive and send request data, receive and send messages, and so on. In some examples, communication unit(s) 304 may include wireless transmitters and receivers that enable computing device 300 to communicate wirelessly with the other computing devices. For instance, in the example of FIG. 3, communication unit(s) 304 include a radio 306 that enables computing device 300 to communicate wirelessly with other computing devices, such as hearing instruments 102 (FIG. 1). Examples of communication unit(s) 304 may include network interface cards, Ethernet cards, optical transceivers, radio frequency transceivers, or other types of devices that are able to send and receive information. Other examples of such communication units may include BLUETOOTH™, 3G, 4G, 5G, and WI-FI™ radios, Universal Serial Bus (USB) interfaces, etc. Computing device 300 may use communication unit(s) 304 to communicate with one or more hearing instruments (e.g., hearing instrument 102 (FIG. 1, FIG. 2)). Additionally, computing device 300 may use communication unit(s) 304 to communicate with one or more other remote devices.

Output device(s) 310 may generate output. Examples of output include tactile, audio, and video output. Output device(s) 310 may include presence-sensitive screens, sound cards, video graphics adapter cards, speakers, liquid crystal displays (LCD), or other types of devices for generating output.

Processor(s) 302 may read instructions from storage device(s) 316 and may execute instructions stored by storage device(s) 316. Execution of the instructions by processor(s) 302 may configure or cause computing device 300 to provide at least some of the functionality ascribed in this disclosure to computing device 300. As shown in the example of FIG. 3, storage device(s) 316 include computer-readable instructions associated with operating system 320, application modules 322A-322N (collectively, "application modules 322"), and a companion application 324. Additionally, in the example of FIG. 3, storage device(s) 316 may store health-related data 326.

Execution of instructions associated with operating system 320 may cause computing device 300 to perform various functions to manage hardware resources of computing device 300 and to provide various common services for other computer programs. Execution of instructions associated with application modules 322 may cause computing device 300 to provide one or more of various applications (e.g., "apps," operating system applications, etc.). Application modules 322 may provide particular applications, such as text messaging (e.g., SMS) applications, instant messaging applications, email applications, social media applications, text composition applications, and so on.

Execution of instructions associated with companion application 324 by processor(s) 302 may cause computing device 300 to perform one or more of various functions. For example, execution of instructions associated with companion application 324 may cause computing device 300 to configure communication unit(s) 304 to receive data from hearing instruments 102 or other sources and use the received data to present data (e.g., health-related data, fitting-related data, etc.) to a user, such as user 104 or a third-party user. In some examples, companion application 324 is an instance of a web application or server application. In some examples, such as examples where computing device 300 is a mobile device or other type of computing device, companion application 324 may be a native application.

Currently, hearing instruments, such as hearing aids, can only be fitted by a hearing healthcare professional. Fitting of a hearing instrument, such as a hearing aid, is a process of adjusting output parameters of the hearing instrument for an individual user. For instance, fitting of a hearing instrument may involve increasing the output levels of a hearing instrument by particular amounts for particular frequency bands, while potentially keeping output levels of the hearing instrument constant at other frequency bands. A fitting of a hearing instrument may refer to the set of output parameters determined by fitting the hearing instrument. Hearing instruments 102 may modify received sound according to the output parameters and receivers of hearing instruments 102 output the received sound for hearing by user 104. For instance, the output parameters may control how hearing instruments 102 amplify the intensity of incoming sound, amplify the intensity of certain frequencies of the incoming sound, translate and/or compress frequencies of the incoming sound, and so on.

Recent legislation from the U.S. Food and Drug Administration (FDA) will begin a new era of providing over-the-counter (OTC) and direct-to-consumer (DTC) hearing aids to hearing-impaired individuals. This presents a challenge of how to ensure users are able to appropriately program their hearing instruments without specialized equipment and a professional. This challenge is especially critical for older users. Many currently-available self-fitting strategies use either preset gain-frequency responses or initial programming based on a hearing test conducted through a web page or mobile application. These hearing tests often require calibration of transducers (headphones or earbuds), which may be a potentially difficult process for older users. Moreover, fine adjustments to meet individual preferences typically require users to manipulate many aspects of sound, such as bass, treble, overall loudness, with a control interface (e.g., a remote control or a mobile app). Without professional guidance, fine adjustments using a control interface across these different aspects of sound may result in sub-optimal or undesirable gain-frequency responses, which may leave users frustrated and unsatisfied.

Some self-fitting hearing instruments (e.g., personal sound amplification products) allow their users to select among a few presets to get something that sounds good to the users. These presets are often based on the degree and configuration of hearing loss, e.g., mild, mild-to-moderate, flat, moderate sloping. Because amplification prescriptions are frequency specific, estimating hearing thresholds via a hearing test is another common strategy that some products implement. Using a mobile app, web portal, or the device itself, speech or pure-tone signals are presented to the listener via a pair of headphones. The results are used to program the hearing instruments. With either a preset or results from a hearing test, a user only gets the initial fitting. Fine adjustments may still be needed to meet individual's needs and preferences. Some hearing instruments allow the manipulation of acoustic parameters in a manner that is common in the audio industry (e.g., through volume controls, equalizer sliders and tone controls), while other hearing instruments provide user interfaces for manipulating multiple variables behind-the-scenes (e.g., gain, frequency response and compression).

Challenges still remain in fitting hearing instruments to individual users. For example, it still may be difficult for users to fit their hearing instruments to their individual preferences. This disclosure describes techniques that may improve the ability of hearing instruments 102 (FIG. 1) to be fitted to individual users. As described herein, the techniques may use one or more self-reported measures to obtain the initial settings and make fine adjustments for individual preferences. Use of the techniques may make it easier for user 104 to fit hearing instruments 102 to the preferences of user 104.

Figure 4:
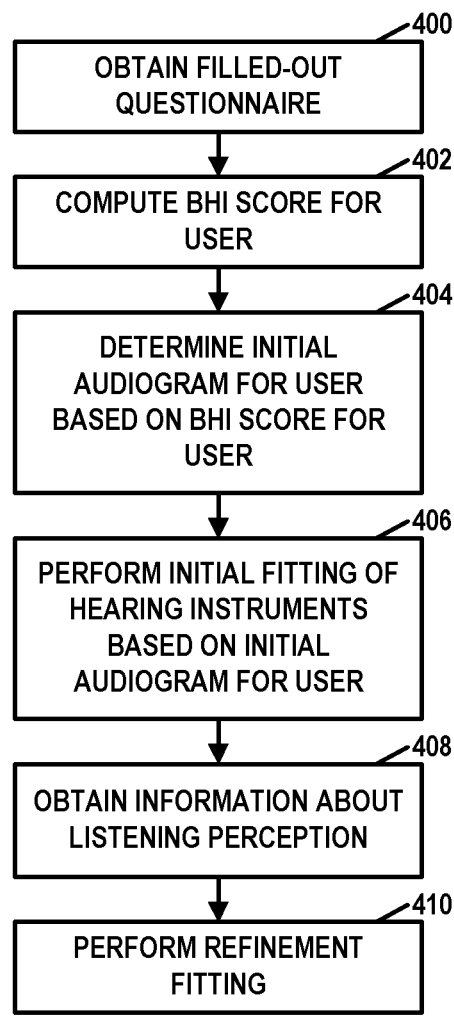
FIG. 4 is a flowchart illustrating an example operation in accordance with one or more aspects of this disclosure.

FIG. 4 is a flowchart illustrating an example operation of a processing system for fitting hearing instruments 102, in accordance with one or more aspects of this disclosure. The flowcharts of this disclosure are provided as examples. Other examples may include more, fewer, or different actions; or actions may be performed in different orders or in parallel. Although FIG. 4 and other parts of this disclosure are discussed as being performed with respect to hearing instruments 102, it is to be understood that much of this discussion is applicable in cases where user 104 only uses a single hearing instrument.

In the example of FIG. 4, a processing system (e.g., one or more processors of hearing instruments 102, one or more processors of computing system 108, processor(s) 208 of hearing instrument 200, processor(s) 302 of computing device 300, or a combination of two or more of these) may perform actions (400) through (406) to determine an initial fitting for hearing instruments 102. In some examples, the determined initial fitting may be the best-possible initial fitting for user 104.

Particularly, in the example of FIG. 4, the processing system may receive data indicating the answers of user 104 to a questionnaire. In some examples, user 104 fills out a questionnaire. For instance, in some examples, companion application 324 may output a user interface for display for user 104 or another user. The user interface may receive indications of user input of the answers to the questionnaire.

An example of such a questionnaire is the Better Hearing Institute (BHI) Quick Hearing Check questionnaire (Kochkin & Bentler, "The validity and reliability of the BHI Quick Hearing Check," *Hearing Review*, 17(12), 12-28 2010 (hereinafter, "Kochkin & Bentler 2010")). The BHI Quick Hearing Check questionnaire is a 15 item, 5-point (0-4) Likert-scaled questionnaire, which has been used to quantify and segment people on subjective hearing loss. The possible questionnaire score range is from 0 to 60. Another example questionnaire may be found at https://hearinghealthmatters.org/waynesworld/2017/hearing-self-test/. For ease of explanation, this disclosure makes reference to the BHI questionnaire and BHI scores, but other questionnaires and scores may apply. In the example of FIG. 4, the processing system may compute, based on the answers of user 104 to the questionnaire, a BHI score for user 104 (402). The processing system may compute the BHI score for user 104 in the standard manner for the BHI questionnaire.

Figure 5:
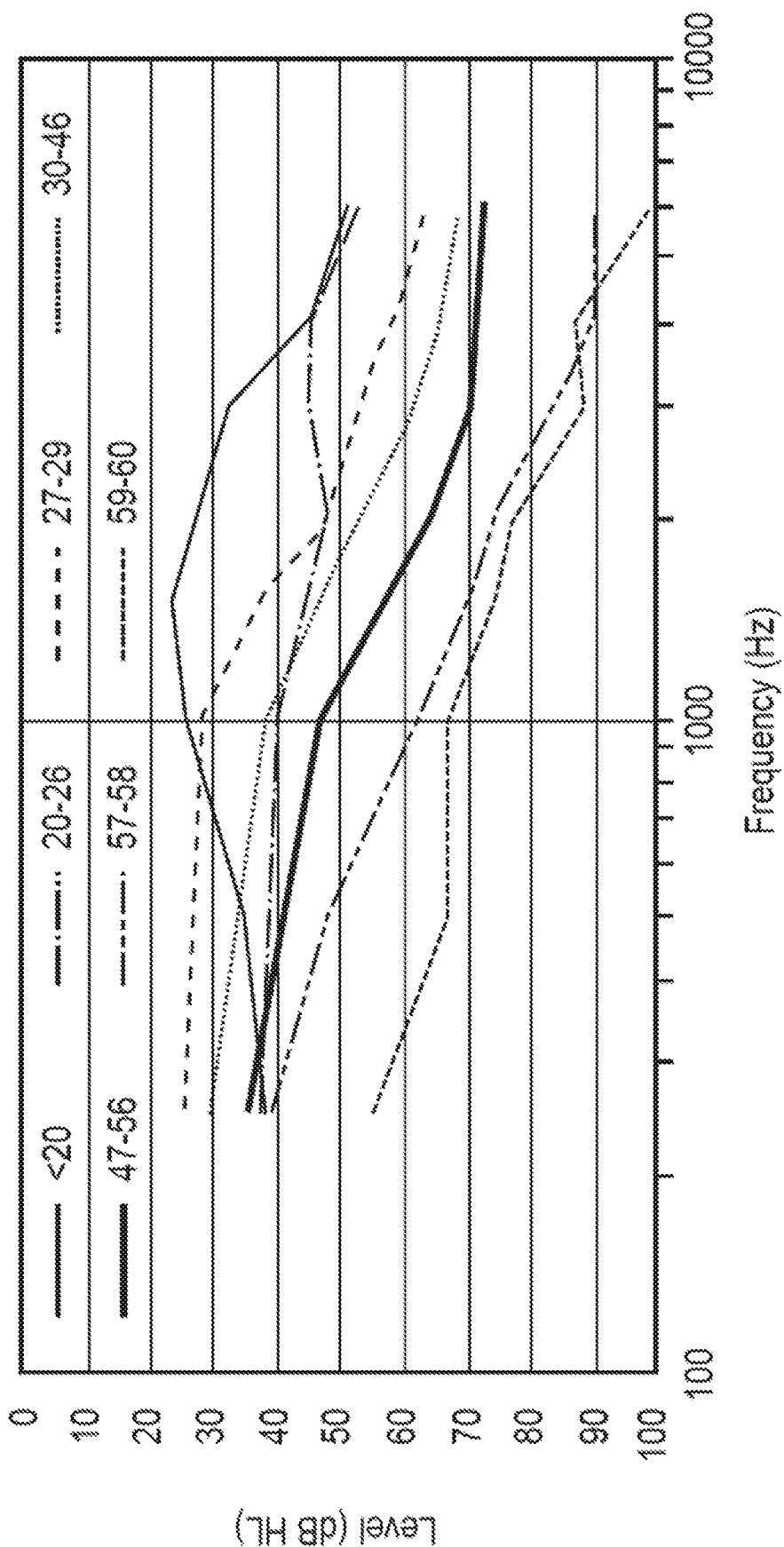
FIG. 5 is a chart illustrating an example direct mapping from Better Hearing Institute (BHI) scores to audiograms.

In some examples, the processing system directly maps the results of the questionnaire to an audiogram. An example of direct mapping between a questionnaire (e.g. the BHI) score and an audiogram is shown in FIG. 5. In other words, FIG. 5 is a chart illustrating an example direct mapping from BHI scores to audiograms. In the example of FIG. 5, differently dashed lines correspond to different audiograms and the different audiograms correspond to different BHI score ranges. The audiograms shown in FIG. 5 and the specific mappings shown are for illustration purposes only, and different audiograms and/or mappings to the BHI results (or the results of some other questionnaire) could be derived.

In other examples, the processing system uses indirect mapping of the results of the questionnaire to an audiogram. For example, the BHI score computed for the user based on the results of the questionnaire may correspond to two or more of audiological test scores. In this case, the "audiological test" may include any of a number of standardized tests, including: 2-, 3-, 4-, 5-, or x-frequency pure-tone averages (PTAs), speech reception thresholds (SRTs), word recognition scores (WRSs), speech recognition in noise scores (e.g., quick speech in noise test scores), otoacoustic emission amplitudes (OAEs), evoked potential results (e.g. auditory brainstem responses (ABRs) (amplitude or latencies), electroencephalogram (EEG) responses) or some other metric.

Thus, in accordance with the techniques of this disclosure, the processing system may map the results of the questionnaire to the results of two or more audiological test results, and may then determine an audiogram that is a best match to those audiological test results based on a calculated distance (e.g., a Euclidean distance, a Manhattan distance, etc.). While direct mapping between questionnaire results and predicted hearing thresholds may be the simpler, indirect mapping may be beneficial in scenarios in which a direct mapping between an individual's questionnaire results and his/her hearing thresholds is not known.

As an example of an indirect mapping, Kochkin S, Bender R., "The validity and reliability of the BHI Quick Hearing Check", *Hearing Review*, 2010; 17(12):12-28, identified a speech reception threshold (SRT) and a five-frequency PTA score (which is an average of hearing thresholds at 500, 1000, 2000, 3000, and 4000 Hz) that correspond to each possible BHI score. Because SRTs are highly correlated with hearing thresholds in the low frequencies (e.g. 500, 1000 and 2000 Hz) (Smoorenburg, "Speech reception in quiet and in noisy conditions by individuals with noise-induced hearing loss in relation to their tone audiogram". *The journal of the acoustical society of America*, 91(1), 421-437 (1992)), SRTs can be assumed to be a proxy for a 3-frequency PTA score. As such, each BHI score can be mapped to a two-dimensional space, with the 3-frequency PTA score corresponding to each score on the x-axis and the 5-frequency PTA score for each BHI score on the y-axis. This allows each BHI score to be compared to the 3-frequency and 5-frequency PTA scores of a set of standard audiograms to determine the closest match. In another example, if the exact relationship between the set of standard audiograms and the SRTs had been established, then SRTs may be plotted directly on the x-axis with 5-frequency PTA scores on the y-axis. However, for the remainder of the disclosure, it is assumed that the SRTs have been converted to 3-frequency PTAs unless otherwise noted.

Sets of standard audiograms have been defined. For example, the International Electrotechnical Commission (IEC) standard provides 60 standard audiograms for hearing aid testing (Bisgaard et al., 2010). In another example, the IEC has also developed a set of 12 standard audiograms and a set of 10 standard audiograms (7 for flat and moderately sloping hearing loss profiles and 3 for steeply sloping hearing loss profiles). In some examples, the standard audiograms are specific to a hearing instrument manufacturer or defined by another standard-setting organization. Each of the possible BHI scores may be mapped to one of the 60 standard audiograms. In the example of FIG. 4, the processing system may determine an initial audiogram for user 104 based on the BHI score for user 104 (404). The initial audiogram for user 104 may be a standard audiogram in a set of standard audiograms. For example, the initial audiogram for user 104 may be one of the 60 standard audiograms defined by the IEC for hearing aid testing. The determined initial audiogram may be an optimal initial audiogram for fitting hearing instruments 102. The processing system may perform initial fitting of hearing instruments 102 based on the initial audiogram for user 104 (406). For instance, the processing system may set output parameters of hearing instruments 102 to compensate for hearing loss associated with the initial audiogram for user 104. In some examples, one or more processors of computing system 108 (e.g., processor(s) 302 of computing device 300) may send the output parameters to hearing instruments 102 (e.g., using communication unit(s) 304 of computing device 300), In some examples, the process for determining the initial audiogram for user 104 is based on a calculated distance (e.g., Euclidean distance, Manhattan distance, etc.) between BHI-estimated PTA scores and standard audiogram PTA scores. In such examples, the processing system calculates the distance between a BHI-estimated PTA score data point for user 104 and the PTA scores of one or more (e.g., each, a plurality, a subset, etc.) of the standard audiograms. The processing system selects the closest standard audiogram to the BHI-estimated PTA score data point for user 104 as the initial audiogram for user 104.

Figure 6:
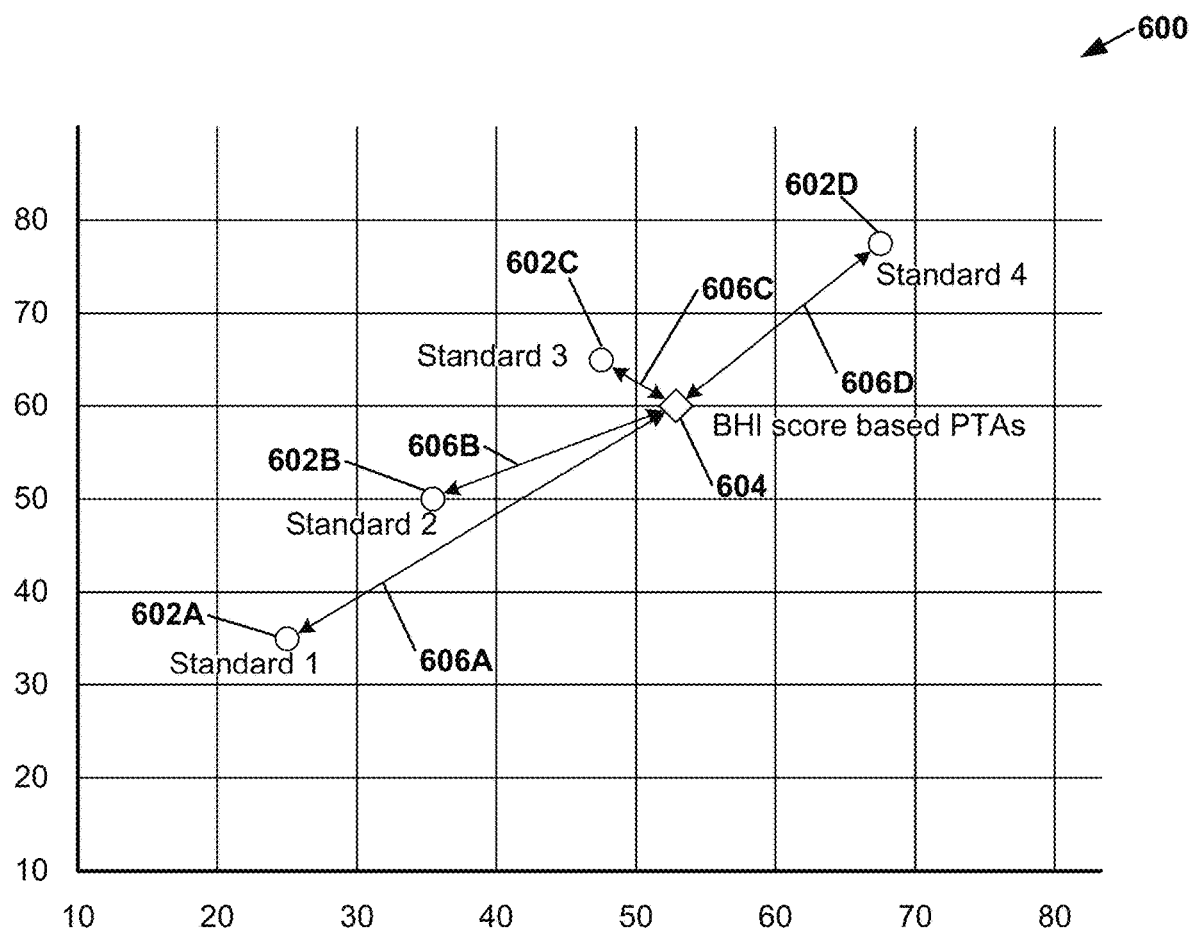
FIG. 6 is a chart conceptually illustrating an initial audiogram for a user based on a BHI score for the user, in accordance with one or more aspects of this disclosure.

FIG. 6 is a chart 600 conceptually illustrating an example for determining an initial audiogram for user 104 based on a BHI score for user 104, in accordance with one or more aspects of this disclosure. One axis of chart 600 corresponds to 3PTA values and the other axis of chart 600 corresponds to 5PTA values. In other examples, one axis of chart 600 may correspond to SRT scores and the other axis of chart 600 corresponds to 5PTA scores. In the example of FIG. 6, points 602A, 602B, 602C, and 602C (collectively, "points 602") correspond to four standard audiograms. In other examples, the processing system may use additional points for additional standard audiograms. Furthermore, in the example of FIG. 6, the chart includes a point 604 (labeled "BHI score-based PTAs") corresponding to the BHI score of user 104.

In the example of FIG. 6, the processing system may calculate the distances 606A-606D (collectively, "distances 606") from the BHI score data point to each of the four standard audiogram data points 602. The distance between the data point 604 for the BHI score and the data point 602C for standard audiogram #3 is the shortest, which means that the hearing loss estimated by the BHI questionnaire is closest to standard audiogram #3. Therefore, a user with these BHI-estimated 3PTA and 5PTA scores (e.g., user 104) may have their hearing instruments (e.g., hearing instruments 102) initially programmed to standard audiogram #3. In the example of FIG. 6, the processing system may map a BHI score to a standard audiogram based on a distance measure. In this example, this BHI score corresponds to a pair of PTA values, which is indicated by a diamond shape. According to distance, standard audiogram #3 has the shortest distance and the processing system uses audiogram #3 for initial fitting.

If more than two or more audiograms are equally distant from the BHI-PTAs (e.g., from point 604), the processing system may determine which of the equally distant audiograms to use. In this disclosure, an audiogram may be considered to have a distance equal to a distance between a point corresponding to the audiogram and a point corresponding to the BHI score data point. In some examples, the processing system makes such a decision based on information about which one of the equally-distant audiograms is more prevalent in a population. In this example, the processing system may use the most prevalent of the equally distant audiograms for initial fitting of hearing instruments 102.

In some examples, the processing system may determine which of the equally distant audiograms to use based on whether user 104 is a new hearing instrument user or is currently a user of a hearing instrument. For instance, if user 104 is currently a user of a hearing instrument, the processing system may select whichever of the equally distant audiograms is a closest match to an audiogram of the user's current hearing instrument. Thus, in some examples, based on a determination that coordinate values for two or more audiograms in the plurality of audiograms are equally distant from the determined coordinate values, the processing system may determine which of the two or more audiograms to use as the initial audiogram based on whether the user is a new hearing instrument user or is currently a hearing instrument user.

In some examples, the processing system may determine which of the equally distant audiograms to use based on responses of a user to one or more additional questions and/or based on a subset of the questions in the questionnaire. In some examples, when two or more of the audiograms are equally distant from the BHI-PTAs, the processing system may determine an average of the two or more equally distant audiograms. The processing system may use the average of the two or more equally-distant audiograms as the initial audiogram for user 104.

Referring back to FIG. 4, after initial programming, the processing system may perform actions (408) and (410) to make fine-tuning adjustments to customize the fitting to the preferences of user 104. For instance, in the example of FIG. 4, the processing system may obtain information about listening perception of sound generated by hearing instruments 102 (408). The processing system may perform a refined fitting based on the information about the listening perception of the sound generated by hearing instruments 102 (410).

Obtaining the information about the listening perception of sound generated by hearing instruments 102 may involve a question-driven automatic adjustment system. User 104 may be asked (e.g., by the processing system, by printed instructions, by a person, etc.) to listen to speech in a quiet situation (e.g., while watching the news at home) and user 104 is then presented with a series of questions. In some examples, a device (e.g., hearing instruments 102, a smartphone of user 104, etc.) may analyze a current acoustic environment of user 104 to help ensure that user 104 is in an appropriately quiet situation. For example, the device may output audio indications of whether user 104 is in an appropriately quiet situation. In some examples, a smartphone may output a sound level meter for display and instruct user 104 to move to or adjust the acoustic environment of user 104 so that user 104 is in an appropriately quiet situation. In some examples, hearing instruments 102 may output an audible indication to user 104 instructing user 104 to move to or adjust the acoustic environment of user 104 so that user 104 is in an appropriately quiet situation. Answers to the questions may correspond to values on numeral scales. In some examples, companion application 324 may output a user interface for display. The user interface presented by companion application 324 may receive indications of user input of the answers to questions regarding the listening perception of the sound generated by hearing instruments 102.

Figures 9, 10:
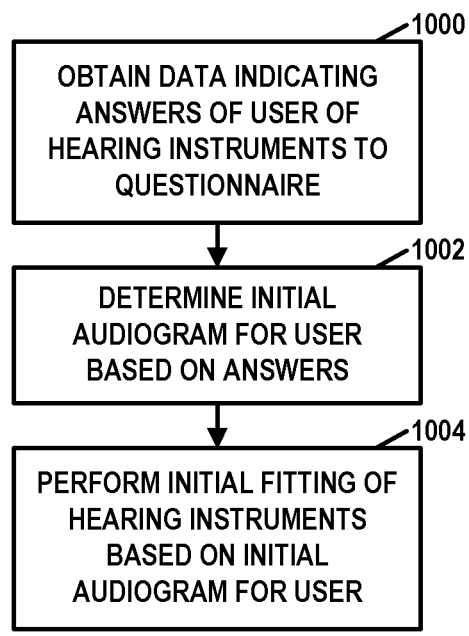
FIG. 9 is an example scale for measuring self-reported clarity, in accordance with one or more aspects of this disclosure.
FIG. 10 is a flowchart illustrating an example operation in accordance with one or more aspects of this disclosure.

FIG. 7 is an example scale for measuring self-reported loudness balance between two ears, accordance with one or more aspects of this disclosure. FIG. 8 is an example scale for measuring self-reported overall loudness, in accordance with one or more aspects of this disclosure. FIG. 9 is an example scale for measuring self-reported clarity, in accordance with one or more aspects of this disclosure.

As shown in the example of FIG. 7, the questions may include one or more questions regarding the loudness balance of sound generated by hearing instruments 102 between the two ears of user 104. As shown in the example of FIG. 8, the questions may include one or more questions regarding overall loudness of sound generated by hearing instruments 102. As shown in the example of FIG. 9, the questions may include questions regarding whether the sound produced by hearing instruments 102 is "tinny" or "boomy" (FIG. 9).

The rating for each of the questions may correspond to predetermined gain changes. For example, if the answer to the question in FIG. 7 indicates that the left ear is "much louder," the processing system may decrease the overall gain of the left hearing instrument by a first predetermined amount (e.g., 3 dB); if the answer to the question of FIG. 7 indicates that the left ear is "slightly louder," the processing system may decrease the overall gain for the left hearing instrument by a second predetermined amount (e.g., 1.5 dB); and so on. Furthermore, in some examples, if the overall loudness rating is "Loud," then the overall gain will be reduced by 3 dB. The user may use these same questions multiple times until the answer to question (1) is "Equally loud," the answer to question (2) is "Comfortable," and the answer to question (3) is "Clear" (neither "tinny" nor "boomy"). With respect to the example of FIG. 9, the processing system may decrease gain for one or more high-frequency bands by a first predetermined amount if the answer is "tinny," by a second predetermined amount if the answer is "slightly tinny"; the processing system may decrease gain for one or more low-frequency bands by a third predetermined amount if the answer is "boomy" and by a fourth predetermined amount if the answer is "slightly boomy." The processing system may receive an indication of the user's response to these questions. In some examples, actions (408) and (410) may be performed multiple times in order to continue refining the fitting for user 104. In some examples, during subsequent performances of actions (408) and (410), the processing system may use different (e.g., smaller, greater) predetermined values. The resulting hearing instrument settings conclude the refined fitting.

Although the BHI questionnaire is used as an example above, the processing system may use the results of other questionnaires to perform this function, so long as the results of the other questionnaires may be mapped to a database of common audiograms.

Furthermore, as an alternative to the standard audiograms, norms may be created by using the actual audiograms from a database of people who have taken the BHI (or another) questionnaire, and these could be used to program the hearing aids. For example, after user 104 has arrived at a refined fitting (e.g., after one or more rounds of actions 408 and 410), the processing system may add an audiogram corresponding to the refined fitting for user 104 to the set of "standard" audiograms. Thus, if another user's BHI score corresponds to PTA values closer to the PTA values corresponding to the BHI score of user 104 than PTA values of other "standard" audiograms, the audiogram corresponding to the refinement fitting for user 104 may be used as the initial audiogram for the other user.

Once the BHI score (or the standard audiogram to which it maps) for user 104 is determined, the result may be used to program hearing instruments 102. There are many ways in which the processing system may determine the BHI score for user 104. For instance, in the following examples, voice recognition may be used:

Hearing instruments 102 may be configured to ask user 104 what his/her BHI score is (or the standard audiogram that it maps to), and he/she responds verbally.

Hearing instruments 102 may be configured to ask user 104 if his/her BHI score (or the standard audiogram # that it maps to) is within a certain range, and user 104 may nod/shake his/her head when the answer is yes; for example:

If the BHI score (or audiogram #) was 33, hearing instruments 102 may ask. "Is the BHI score (or audiogram #) 0-9?" (User 104 may either shake his/her head no or makes no response.) After a few seconds, hearing instruments 102 may ask "Is the BHI score (or audiogram #) 10-19?" (User 104 then either shakes his/her head no or makes no response.) After a few seconds, hearing instruments 102 may ask "Is the BHI score (or audiogram #) 20-29?" (User 104 either shakes his/her head no or makes no response.) After a few seconds, hearing instruments 102 may ask "Is the BHI score (or audiogram #) 30-39?" (User 104 nods yes.) Hearing instruments 102 may then perform a similar process until the correct exact audiogram number is identified.

Potentially, ranges for the most common BHI scores (or audiograms) could be listed first to minimize the number of responses that most people need to give.

In some examples, hearing instruments 102 may ask user 104 if his/her BHI score (or the standard audiogram that it maps to) is within a certain range, and user 104 may press a button on hearing instruments 102 when the answer is yes (following the example above). In some examples, hearing instruments 102 ask user 104 if his/her BHI score (or the standard audiogram that it maps to) is within a certain range, and user 104 taps on hearing instruments 102 (e.g. via a double tap) when the answer is yes (following the example above).

In some examples, presets are programmed into hearing instruments 102 and user 104 navigates to (e.g. via a manual control) a given preset; he/she then performs some function (e.g., pushing and holding a button) to save that preset into hearing instruments 102. If many presets exist, user 104 may have the option of scrolling through presets quickly (e.g., by using a rotary wheel or holding down a button).

In some examples, user 104 uses a remote control to enter the results of the BHI questionnaire (or the audiogram that it maps to). The remote control may communicate with hearing instruments 102 to program hearing instruments 102.

In some examples, user 104 completes the questionnaire within an application (e.g., a native application, a web application, etc.) that automatically programs hearing instruments 102 based on the results. In some examples, user 104 completes a paper-and-pencil questionnaire and then enters the result into an application (e.g., a native application, a web application, etc.). In this way, the processing system may obtain data indicating answers to the questionnaire.

Although "boomy" and "tinny" are used in the present example, other descriptors representing high-frequency and low-frequency gain changes may also be used (e.g. treble/bass, sharpness/fullness, etc.).

User 104 may be presented with the fine-tuning question using any of the interfaces listed above (e.g., a speech interface, a remote control or an app on a computer or other smart device). User 104 may respond to the fine-tuning questions using any of the options outlined above (e.g., a speech recognition, head gestures, manual controls on the hearing aids, tapping the hearing aids, a remote control or an app on a smartphone, tablet, watch, computer or other smart device).

In some examples, refined settings from OTC/DTC users are stored in the cloud. Thus, each BHI score may correspond to a number of refined settings. The initial programming could be optimized by considering all the available refined settings for a given BHI score.

FIG. 10 is a flowchart illustrating an example operation in accordance with one or more aspects of this disclosure. FIG. 10 may be considered a more general case of FIG. 4. In the example of FIG. 10, a processing system (e.g., one or more processors of hearing instruments 102, one or more processors of computing system 108, processor(s) 208 of hearing instrument 200, processor(s) 302 of computing device 300, or a combination of two or more of these) may perform actions (1000) through (1004) to determine an initial fitting for hearing instruments 102.

In the example of FIG. 10, the processing system may obtain data indicating answers of user 104 of hearing instruments 102 to a questionnaire (1000). For example, the processing system may obtain data indicating the answers of user 104 to a BHI questionnaire or another hearing assessment questionnaire.

Furthermore, in the example of FIG. 10, the processing system may determine an initial audiogram based on the answers (1002). For instance, the processing system may determine the initial audiogram for user 104 based on a BHI score for user 104. More generally, in some examples, as part of determining the initial audiogram based on the answers, the processing system may determine a score (e.g., a BHI score) corresponding to the answers of user 104. In such examples, the processing system may determine coordinate values corresponding to the score. For instance, the processing system may determine a pair of PTA values (e.g., a three-frequency PTA value and a five-frequency PTA value) corresponding to the score. In another example, the processing system may determine the coordinate value by determining a SRT value and a 5PTA value corresponding to the score. Furthermore, in such examples, the processing system may determine the initial audiogram based on distances between the coordinate values and coordinate values for a plurality of audiograms.

In some examples, such as the example of FIG. 6, to determine the initial audiogram based on the distances between the coordinate values and the coordinate values for the plurality of audiograms, the processing system may, for each respective audiogram of the plurality of audiograms, calculate a respective distance (e.g., one of distances 606) for the respective audiogram. The respective distance for the respective audiogram is a distance between a first point (e.g., point 604) and a respective point for the respective audiogram (e.g., one of points 602). The first point has the coordinate values that correspond to the score corresponding to the answers. The respective point for the respective audiogram having the coordinate values for the respective audiogram. Furthermore, the processing system may determine a shortest distance among the distances for the plurality of audiograms. The processing system may determine the initial audiogram based on a closest audiogram in the plurality of audiograms. The distance for the closest audiogram is equal to the shortest distance among the distances for the plurality of audiograms. For instance, the processing system may determine that the initial audiogram is the closest audiogram.

In some examples, the processing system may determine a plurality of closest audiograms in the plurality of audiograms. In such examples, the distances for each of the closest audiograms are equal to the shortest distance among the distances for the plurality of audiograms. Furthermore, in such examples, the processing system may select the initial audiogram from among the plurality of closest audiograms based on which one of the closest audiograms is more prevalent in a population. For instance, the processing system may retrieve and compare stored data indicating prevalence values for the audiograms.

In some examples, the processing system may determine a plurality of closest audiograms in the plurality of audiograms. In such examples, the distances for each of the closest audiograms are equal to the shortest distance among the distances for the plurality of audiograms. In such examples, the processing system may determine an average of the plurality of closest audiograms. For instance, the processing system may determine, for each frequency band of the closest audiograms, an average of the thresholds for the frequency band. The processing system may use the average of the plurality of closest audiograms as the initial audiogram.

In some examples, to determine the initial audiogram, the processing system may identify, based on the answers, multiple audiograms from a set of audiograms, such as a set of standard audiograms. The processing system may then determine the initial audiogram based on the multiple identified audiograms. For instance, the processing system may assign thresholds from the identified audiograms to different frequency bands of the initial audiogram.

For example, the processing system may identify a first audiogram based on distances between the 3PTA score for user 104 and 3PTA values of the standard audiograms. In this example, the first audiogram has a closer 3PTA value to the 3PTA score for user 104 than the other standard audiograms. For ease of explanation, this disclosure may refer to this first audiogram as a 3PTA audiogram. Additionally, in this example, the processing system may identify a second audiogram based on distances between the 5PTA score for user 104 and 5PTA values of the standard audiograms. In this example, the second audiogram has a closer 5PTA value to the 5PTA score for user 104 than the other standard audiograms. For ease of explanation, this disclosure may refer to this second audiogram as a 5PTA audiogram. Furthermore, in this example, the processing system may assign the 500 Hz, 1000 Hz, and 2000 Hz thresholds of the 3PTA audiogram as the 500 Hz, 1000 Hz, and 1000 Hz thresholds of the initial audiogram, and may assign the 3000 Hz and 4000 Hz thresholds of the 5PTA audiogram as the 3000 Hz and 4000 Hz thresholds of the initial audiogram.

In another example, the processing system may identify an audiogram from among the standard audiograms. For instance, in this example, the identified standard audiogram may have a closer 3PTA value to the 3PTA score for user 104 than any of the other standard audiograms. In other instances, the identified standard audiogram may have a closer 5PTA value to the 5PTA score for user 104 than any of the other standard audiograms. In still other instances, a Euclidean distance from the 3PTA and 5PTA values of the identified standard audiogram is closer to the 3PTA and 5PTA scores for user 104 than any of the other standard audiograms. Like in the previous example, the processing system may assign the 500 Hz, 1000 Hz, and 2000 Hz thresholds of the identified standard audiogram as the 500 Hz, 1000 Hz, and 1000 Hz thresholds of the initial audiogram. However, in this example, the processing system may determine an average of the 3000 Hz and 4000 Hz thresholds of the identified standard audiogram, e.g., using the following formula:

$$((5\text{-frequency PTA}*5)-(3\text{-frequency PTA}*3))/2 = (3000\text{ Hz hearing threshold}+4000\text{ Hz hearing thresholds})/2$$

In the formula above, "3-frequency PTA" denotes an average of the thresholds of the identified standard audiogram for 500, 1000, and 2000 Hz and "5-frequency PTA" denotes an average of the thresholds of the identified standard audiogram for 500, 1000, 2000, 3000, and 4000 Hz. As noted in the formula above, subtracting 3-frequency PTA*3 from 5-frequency PTA*5 and dividing by two is equivalent to the average of the 3000 and 4000 Hz thresholds of the identified standard audiogram. In this example, the processing system may use the average value of the 3000 Hz and 4000 Hz thresholds of the identified standard audiogram and the slope of the identified standard audiogram to determine values of the 3000 Hz and 4000 Hz thresholds of the initial audiogram. For instance, in one such example, consider the situation in which the processing system has used the formula above and determined that the mean hearing threshold at 3000 and 4000 Hz is 60 dB HL. HL in this context refers to hearing loss. The processing system may then use this information to more precisely set the 3000 Hz and 4000 Hz thresholds of the initial audiogram.

In some examples, the processing system may do so by determining a slope of the thresholds of the identified standard audiogram. The processing system, may then consider the averaged threshold value as corresponding to a point between 3000 Hz and 4000 Hz (e.g., 3500 Hz or another value). The processing system may then extrapolate the 3000 Hz and 4000 Hz thresholds of the initial audiogram based on the calculated average value and the determined slope. For example, if the identified standard audiogram has a flat loss (i.e., the slope of the identified standard audiogram is small), the processing system may set each of the 3000 Hz and 4000 Hz thresholds of the initial audiogram to 60 dB HL. However, if the identified standard audiogram has a steep slope, the processing system may set the 3000 Hz threshold of the initial audiogram to 45 dB HL and the 4000 Hz threshold of the initial audiogram to 75 dB HL. In each of the above examples, frequency bands other than 500, 1000, 2000, 3000, and 4000 Hz may be used.

In this way, the processing system may determine an average of a first frequency threshold 3000 Hz) of the initial audiogram and a second frequency threshold (e.g., 4000 Hz) of the initial audiogram. Furthermore, the processing system may determine a slope for thresholds of the initial audiogram. The thresholds of the initial audiogram include the first and second frequency thresholds of the initial audiogram. In this example, the processing system may extrapolate, based on the average of the first and second frequency thresholds and the slope, refined values for the first and second frequency thresholds. The processing system may set the first and second frequency thresholds of the initial audiogram to the refined values for the first and second frequency thresholds, respectively.

In the example of FIG. 10, the processing system may perform an initial fitting of the one or more hearing instruments based on the initial audiogram (1004). For instance, in examples where the processing system is implemented in computing system 108, the processing system may send (e.g., using one or more of communication unit(s) 304) instructions to set output parameters of hearing instruments 102 based on the initial audiogram. In examples where the processing system is implemented in hearing instruments 102, hearing instruments 102 may update output parameters of hearing instruments 102 (e.g., by changing stored values of the output parameters in storage device(s) 202) based on the initial audiogram.

As noted elsewhere in this disclosure, after user 104 has arrived at a refined fitting (e.g., after one or more rounds of actions 408 and 410 in FIG. 4), the processing system may add an audiogram corresponding to the refined fitting for user 104 to the set of "standard" audiograms and associate the audiogram corresponding to the refined fitting with the 3- and 5-frequency PTAs corresponding to initially assessed the BHI score for user 104. In such examples, the processing system may obtain information about listening perception of sound generated by the one or more first hearing instruments. The processing system may perform a refined fitting of the one or more first hearing instruments based on the information about the listening perception of the sound generated by the one or more first hearing instruments. The processing system may include an audiogram corresponding to the refined fitting of the one or more first hearing instruments in the plurality of audiograms. Subsequently, the processing system may perform a second iteration of this process with another, second user. Thus, if the second user has a BHI score similar to the BHI score for user 104, the audiogram corresponding to the refined fitting may be determined as an initial audiogram for the second user.

Thus, the hearing instruments, the user, answers, and score associated with the earlier iteration may be referred to as the first hearing instruments, first user, first answers, and first score. For instance, after including the audiogram corresponding to the refined fitting of the one or more first hearing instruments in the plurality of audiograms, the processing system may obtain data indicating answers of a second user of one or more second hearing instruments to the questionnaire. The second hearing instruments are different and separate from the first hearing instruments. The questionnaire may be the same as in the first iteration. The processing system may determine a second score, where the second score corresponds to the answers of the second user. The processing system may determine the second score in the same manner that the processing system determined the first score. Furthermore, the processing system may determine coordinate values corresponding to the second score. The processing system may determine the coordinate values corresponding to the second score in the same way as the first score. The processing system may determine a second initial audiogram based on distances between the coordinate values corresponding to the second score and coordinate values for the plurality of audiograms. In addition, the processing system may perform an initial fitting of the one or more second hearing instruments based on the second initial audiogram.

In the context of FIG. 10, after the processing system performs the initial fitting of one or more hearing instruments, the processing system may obtain information about listening perception of sound generated by the one or more hearing instruments 102. In this example, the processing system may perform a refined fitting based on the information about the listening perception of the sound generated by the one or more hearing instruments 102. In some such examples, the answers to the questionnaire may be a first set of answers and, as part of obtaining information about listening perception of sound generated by the one or more hearing instruments 102, the processing system may obtain a second set of answers. The second set of answers are responses of the first user to questions regarding the listening perception of the sound generated by the one or more hearing instruments 102 after performing the initial fitting of the one or more hearing instruments 102. The questions regarding the listening perception of the sound generated by the one or more hearing instruments 102 include one or more of: questions regarding an overall loudness of sound generated by the one or more hearing instruments 102, questions regarding a loudness balance of the sound generated by the one or more hearing instruments 102 when the one or more hearing instruments 102 include two hearing instruments, or questions regarding whether the sound generated by the one or more hearing instruments 102 is tinny or boomy.

The following is a non-limiting list of examples that are in accordance with one or more techniques of this disclosure.

EXAMPLE 1

A method comprising: obtaining, by a processing system, data indicating answers of a user of one or more hearing instruments to a questionnaire; determining, by the processing system, an initial audiogram based on the answers; and performing, by the processing system, an initial fitting of the one or more hearing instruments based on the initial audiogram.

EXAMPLE 2

The method of example 1, wherein determining the initial audiogram based on the answers comprises: determining, by the processing system, a score corresponding to the answers; determining, by the processing system, coordinate values corresponding to the score; and determining, by the processing system, the initial audiogram based on distances between the coordinate values and coordinate values for a plurality of audiograms.

EXAMPLE 3

The method of example 2, wherein determining the coordinate values comprises determining a pair of pure-tone-average (PTA) values corresponding to the score.

EXAMPLE 4

The method of example 3, wherein the pair of PTA values includes a three-frequency PTA value and a five-frequency PTA value.

EXAMPLE 5

The method of example 2, wherein determining the coordinate values comprises determining a Speech Recognition Threshold (SRT) value and a five-frequency PTA value.

EXAMPLE 6

The method of any of examples 2-5, wherein determining the initial audiogram based on the distances between the coordinate values and the coordinate values for the plurality of audiograms comprises: for each respective audiogram of the plurality of audiograms, calculating, by the processing system, a respective distance for the respective audiogram, the respective distance for the respective audiogram being a distance between a first point and a respective point for the respective audiogram, the first point having the coordinate values that correspond to the score corresponding to the answers, the respective point for the respective audiogram having the coordinate values for the respective audiogram; determining, by the processing system, a shortest distance among the distances for the plurality of audiograms; and determining, by the processing system, the initial audiogram based on a closest audiogram in the plurality of audiograms, wherein the distance for the closest audiogram is equal to the shortest distance among the distances for the plurality of audiograms.

EXAMPLE 7

The method of example 6, wherein the initial audiogram is the closest audiogram.

EXAMPLE 8

The method of example 6, wherein determining the initial audiogram based on the closest audiogram comprises: determining, by the processing system, a plurality of closest audiograms in the plurality of audiograms includes, wherein the distances for each of the closest audiograms are equal to the shortest distance among the distances for the plurality of audiograms; and selecting, by the processing system, the initial audiogram from among the plurality of closest audiograms based on which one of the closest audiograms is more prevalent in a population.

EXAMPLE 9

The method of example 6, wherein determining the initial audiogram based on the closest audiogram comprises: determining, by the processing system, that the plurality of audiograms includes a plurality of closest audiograms, wherein the distances for each of the closest audiograms are equal to the shortest distance among the distances for the plurality of audiograms; and determining, by the processing system, an average of the plurality of closest audiograms; and using, by the processing system, the average of the plurality of closest audiograms as the initial audiogram.

EXAMPLE 10

The method of any of examples 2-9, wherein the user is a first user, the one or more hearing instruments are one or more first hearing instruments, and the method further comprises: obtaining, by the processing system, information about listening perception of sound generated by the one or more first hearing instruments; performing, by the processing system, a refined fitting of the one or more first hearing instruments based on the information about the listening perception of the sound generated by the one or more first hearing instruments; and including, by the processing system, an audiogram corresponding to the refined fitting of the one or more first hearing instruments in the plurality of audiograms; and after including the audiogram corresponding to the refined fitting of the one or more first hearing instruments in the plurality of audiograms: obtaining, by the processing system, data indicating answers of a second user of one or more second hearing instruments to the questionnaire; determining, by the processing system, a second score, the second score corresponding to the answers of the second user; determining, by the processing system, coordinate values corresponding to the second score; determining, by the processing system, a second initial audiogram based on distances between the coordinate values corresponding to the second score and coordinate values for the plurality of audiograms; and performing, by the processing system, an initial fitting of the one or more second hearing instruments based on the second initial audiogram.

EXAMPLE 11

The method of any of examples 1-9, wherein the user is a first user, the one or more hearing instruments are one or more first hearing instruments, and the method further comprises, after performing the initial fitting of the one or more first hearing instruments: obtaining, by the processing system, information about listening perception of sound generated by the one or more first hearing instruments; and performing, by the processing system, a refined fitting based on the information about the listening perception of the sound generated by the one or more first hearing instruments.

EXAMPLE 12

The method of example 10 or 11, wherein: the answers are a first set of answers, and obtaining information about listening perception of sound generated by the one or more first hearing instruments comprises obtaining, by the processing system, a second set of answers, the second set of answers being responses of the first user to questions regarding the listening perception of the sound generated by the one or more first hearing instruments after performing the initial fitting of the one or more first hearing instruments.

EXAMPLE 13

The method of example 10 or 11, wherein the questions regarding the listening perception of the sound generated by the one or more first hearing instruments include one or more of: questions regarding an overall loudness of sound generated by the one or more first hearing instruments, questions regarding a loudness balance of the sound generated by the one or more first hearing instruments when the one or more first hearing instruments include two hearing instruments, or questions regarding whether the sound generated by the one or more first hearing instruments is tinny or boomy.

EXAMPLE 14

The method of any of examples 1-13, wherein determining the initial audiogram comprises: identifying, based on the answer, multiple audiograms from a set of audiograms; and determining the initial audiogram based on the multiple identified audiograms.

EXAMPLE 15

A computing system comprising: one or more computing devices, wherein one or more processors and one or more communication units are included in the one or more computing devices, the one or more communication units are configured to communicate with one or more hearing instruments, and the one or more processors are configured to: obtain data indicating answers of a user of the one or more hearing instruments to a questionnaire; determine an initial audiogram based on the answers; and perform an initial fitting of the one or more hearing instruments based on the initial audiogram.

EXAMPLE 16

The computing system of example 15, wherein the one or more processors are configured to perform the methods of any of examples 1-14.

EXAMPLE 17

A hearing instrument comprising: one or more processors configured to: obtain data indicating answers of a user of the one or more hearing instruments to a questionnaire; determine an initial audiogram based on the answers; and perform an initial fitting of the hearing instrument based on the initial audiogram; and a receiver comprising one or more speakers for generating audible sound.

EXAMPLE 18

The hearing instrument of examples 15, wherein the one or more processors are configured to perform the methods of any of examples 1-14.

EXAMPLE 19

A processing system comprising means for performing the methods of any of examples 1-14.

EXAMPLE 20

The processing system of example 19, wherein the processing system includes one or more hearing instruments.

EXAMPLE 21

A computer-readable data storage medium having instructions stored thereon that when executed cause a processing system to perform the methods of any of examples 1-14.

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations. Furthermore, with respect to examples that involve personal data regarding a user, it may be required that such personal data only be used with the permission of the user.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
   obtaining, by a processing system, data indicating answers of a user of one or more hearing instruments to a questionnaire;
   determining, by the processing system, an initial audiogram based on the answers, wherein determining the initial audiogram based on the answers comprises:
      determining, by the processing system, a score corresponding to the answers;
      determining, by the processing system, coordinate values corresponding to the score; and
      determining, by the processing system, the initial audiogram based on distances between the determined coordinate values and coordinate values for a plurality of audiograms; and
   performing, by the processing system, an initial fitting of the one or more hearing instruments based on the initial audiogram, wherein performing the initial fitting comprises setting, by the processing system, output parameters of the one or more hearing instruments to compensate for hearing loss associated with the initial audiogram.

2. The method of claim 1, wherein determining the coordinate values corresponding to the score comprises determining a pair of pure-tone-average (PTA) values corresponding to the score.

3. The method of claim 2, wherein the pair of PTA values includes a three-frequency PTA value and a five-frequency PTA value.

4. The method of claim 1, wherein determining the coordinate values corresponding to the score comprises determining a Speech Recognition Threshold (SRT) value and a five-frequency PTA value.

5. The method of claim 1, wherein determining the initial audiogram comprises:
   responsive to a determination that coordinate values for two or more audiograms in the plurality of audiograms are equally distant from the determined coordinate values corresponding to the score, determining which of the two or more audiograms to use as the initial audiogram based on whether the user is a new hearing instrument user or is currently a hearing instrument user.

6. The method of claim 1, wherein determining the initial audiogram comprises:
   for each respective audiogram of the plurality of audiograms, calculating, by the processing system, a respective distance for the respective audiogram, the respective distance for the respective audiogram being a distance between a first point and a respective point for the respective audiogram, the first point having the coordinate values corresponding to the score, the respective point for the respective audiogram having the coordinate values for the respective audiogram;
   determining, by the processing system, a shortest distance among the distances for the plurality of audiograms; and
   determining, by the processing system, the initial audiogram based on a closest audiogram in the plurality of audiograms, wherein the distance for the closest audiogram is equal to the shortest distance among the distances for the plurality of audiograms.

7. The method of claim 6, wherein the initial audiogram is the closest audiogram.

8. The method of claim 7, wherein determining the initial audiogram based on the closest audiogram comprises:
   determining, by the processing system, a plurality of closest audiograms in the plurality of audiograms includes, wherein the distances for each of the closest audiograms are equal to the shortest distance among the distances for the plurality of audiograms; and
   selecting, by the processing system, the initial audiogram from among the plurality of closest audiograms based on which one of the closest audiograms is more prevalent in a population.

9. The method of claim 6, wherein determining the initial audiogram based on the closest audiogram comprises:
   determining, by the processing system, that the plurality of audiograms includes a plurality of closest audiograms, wherein the distances for each of the closest audiograms are equal to the shortest distance among the distances for the plurality of audiograms;
   determining, by the processing system, an average of the plurality of closest audiograms; and
   using, by the processing system, the average of the plurality of closest audiograms as the initial audiogram.

10. The method of claim 1, wherein the user is a first user, the one or more hearing instruments are one or more first hearing instruments, and the method further comprises:
    obtaining, by the processing system, information about listening perception of sound generated by the one or more first hearing instruments;
    performing, by the processing system, a refined fitting of the one or more first hearing instruments based on the information about the listening perception of the sound generated by the one or more first hearing instruments;
    including, by the processing system, an audiogram corresponding to the refined fitting of the one or more first hearing instruments in the plurality of audiograms; and
    after including the audiogram corresponding to the refined fitting of the one or more first hearing instruments in the plurality of audiograms:
       obtaining, by the processing system, data indicating answers of a second user of one or more second hearing instruments to the questionnaire;
       determining, by the processing system, a second score, the second score corresponding to the answers of the second user;
       determining, by the processing system, coordinate values corresponding to the second score;
       determining, by the processing system, a second initial audiogram based on distances between the coordinate values corresponding to the second score and coordinate values for the plurality of audiograms; and
       performing, by the processing system, an initial fitting of the one or more second hearing instruments based on the second initial audiogram, wherein the processing system is configured to, as part of performing the initial fitting of the one or more second hearing instruments, set output parameters of the one or more second hearing instruments to compensate for hearing loss associated with the second initial audiogram.

11. The method of claim 1, wherein the user is a first user, the one or more hearing instruments are one or more first hearing instruments, and the method further comprises, after performing the initial fitting of the one or more first hearing instruments:
    obtaining, by the processing system, information about listening perception of sound generated by the one or more first hearing instruments; and
    performing, by the processing system, a refined fitting based on the information about the listening perception of the sound generated by the one or more first hearing instruments.

12. The method of claim 11, wherein:
    the answers are a first set of answers, and
    obtaining the information about the listening perception of the sound generated by the one or more first hearing instruments comprises obtaining, by the processing system, a second set of answers, the second set of answers being responses of the first user to questions regarding the listening perception of the sound generated by the one or more first hearing instruments after performing the initial fitting of the one or more first hearing instruments.

13. The method of claim 12, wherein the questions regarding the listening perception of the sound generated by the one or more first hearing instruments include one or more of:
    questions regarding an overall loudness of sound generated by the one or more first hearing instruments,
    questions regarding a loudness balance of the sound generated by the one or more first hearing instruments when the one or more first hearing instruments include two hearing instruments, or
    questions regarding whether the sound generated by the one or more first hearing instruments is tinny or boomy.

14. The method of claim 1, wherein determining the initial audiogram comprises:
    identifying, based on the answers, multiple audiograms from a set of audiograms; and
    determining the initial audiogram based on the multiple identified audiograms.

15. The method of claim 1, further comprising:
    determining, by the processing system, an average of a first frequency threshold of the initial audiogram and a second frequency threshold of the initial audiogram;
    determining, by the processing system, a slope for thresholds of the initial audiogram, wherein the thresholds of the initial audiogram include the first and second frequency thresholds of the initial audiogram;
    extrapolating, by the processing system, based on the average of the first and second frequency thresholds and the slope, refined values for the first and second frequency thresholds; and
    setting, by the processing system, the first and second frequency thresholds of the initial audiogram to the refined values for the first and second frequency thresholds, respectively.

16. A computing system comprising:
    one or more computing devices, wherein one or more processors and one or more communication units are included in the one or more computing devices, the one or more communication units are configured to communicate with one or more hearing instruments, and the one or more processors are configured to:
       obtain data indicating answers of a user of the one or more hearing instruments to a questionnaire;
       determine an initial audiogram based on the answers, wherein the one or more processors are configured such that, as part of determining the initial audiogram based on the answers, the one or more processors:

determine a score corresponding to the answers;

determine coordinate values corresponding to the score; and determine the initial audiogram based on distances between the determined coordinate values corresponding to the score and coordinate values for a plurality of audiograms; and perform an initial fitting of the one or more hearing instruments based on the initial audiogram, wherein the one or more processors are configured to, as part of performing the initial fitting, set output parameters of the one or more hearing instruments to compensate for hearing loss associated with the initial audiogram.

17. The computing system of claim 16, wherein the one or more processors are configured to, as part of determining the initial audiogram:

for each respective audiogram of the plurality of audiograms, calculate a respective distance for the respective audiogram, the respective distance for the respective audiogram being a distance between a first point and a respective point for the respective audiogram, the first point having the coordinate values corresponding to the score, the respective point for the respective audiogram having the coordinate values for the respective audiogram;

determine a shortest distance among the distances for the plurality of audiograms; and determine the initial audiogram based on a closest audiogram in the plurality of audiograms, wherein the distance for the closest audiogram is equal to the shortest distance among the distances for the plurality of audiograms.

18. The computing system of claim 16, wherein the user is a first user, the one or more hearing instruments are one or more first hearing instruments, and the one or more processors are further configured to:

obtain information about listening perception of sound generated by the one or more first hearing instruments;

perform a refined fitting of the one or more first hearing instruments based on the information about the listening perception of the sound generated by the one or more first hearing instruments;

include an audiogram corresponding to the refined fitting of the one or more first hearing instruments in the plurality of audiograms; and after including the audiogram corresponding to the refined fitting of the one or more first hearing instruments in the plurality of audiograms:

obtain data indicating answers of a second user of one or more second hearing instruments to the questionnaire;

determine a second score, the second score corresponding to the answers of the second user;

determine coordinate values corresponding to the second score;

determine a second initial audiogram based on distances between the coordinate values corresponding to the second score and coordinate values for the plurality of audiograms; and perform an initial fitting of the one or more second hearing instruments based on the second initial audiogram, wherein the one or more processors are configured to, as part of performing the initial fitting of the one or more second hearing instruments, set output parameters of the one or more second hearing instruments to compensate for hearing loss associated with the second initial audiogram.

19. A hearing instrument comprising:

one or more processors configured to:

obtain data indicating answers of a user of the hearing instrument to a questionnaire;

determine an initial audiogram based on the answers, wherein the one or more processors are configured such that, as part of determining the initial audiogram based on the answers, the one or more processors:

determine a score corresponding to the answers;

determine coordinate values corresponding to the score; and determine the initial audiogram based on distances between the determined coordinate values corresponding to the score and coordinate values for a plurality of audiograms; and perform an initial fitting of the hearing instrument based on the initial audiogram, wherein the one or more processors are configured to, as part of performing the initial fitting, set output parameters of the hearing instrument to compensate for hearing loss associated with the initial audiogram; and a receiver comprising one or more speakers for generating audible sound.

20. The hearing instrument of claim 19, wherein the one or more processors are configured to, as part of determining the initial audiogram:

for each respective audiogram of the plurality of audiograms, calculate a respective distance for the respective audiogram, the respective distance for the respective audiogram being a distance between a first point and a respective point for the respective audiogram, the first point having the coordinate values corresponding to the score, the respective point for the respective audiogram having the coordinate values for the respective audiogram;

determine a shortest distance among the distances for the plurality of audiograms; and determine the initial audiogram based on a closest audiogram in the plurality of audiograms, wherein the distance for the closest audiogram is equal to the shortest distance among the distances for the plurality of audiograms.

* * * * *